United States Patent [19]

Lix

[11] Patent Number: 4,952,208
[45] Date of Patent: Aug. 28, 1990

[54] INJECTION SYRINGE FOR MEDICAL PURPOSES

[75] Inventor: Helmut Lix, Wasserburg, Fed. Rep. of Germany

[73] Assignee: Wasserburger Arzneimittelwerk Dr. Madaus GmbH & Co. KG, Fed. Rep. of Germany

[21] Appl. No.: 227,185

[22] Filed: Jul. 22, 1988

[30] Foreign Application Priority Data

Jul. 21, 1987 [DE] Fed. Rep. of Germany ....... 3724120
May 18, 1988 [DE] Fed. Rep. of Germany ....... 3816961

[51] Int. Cl.⁵ ............................................... A61M 5/00
[52] U.S. Cl. ..................................... 604/187; 604/221; 604/218
[58] Field of Search ................. 604/187, 221, 218, 56, 604/82, 89, 90, 91, 311

[56] References Cited

U.S. PATENT DOCUMENTS

| | | | |
|---|---|---|---|
| 2,591,046 | 4/1952 | Brown | 604/90 |
| 2,717,601 | 9/1955 | Brown | 604/90 |
| 3,255,752 | 6/1966 | Dick | 604/89 |
| 4,496,344 | 1/1985 | Kamstra | 604/90 |
| 4,540,410 | 9/1985 | Wood et al. | 604/56 |
| 4,599,082 | 7/1986 | Grimard | 604/90 |
| 4,690,154 | 9/1987 | Woodford et al. | 128/765 |

FOREIGN PATENT DOCUMENTS

| | | | |
|---|---|---|---|
| 0248016 | 7/1966 | Austria | 604/218 |
| 0683694 | 2/1965 | Italy | 604/218 |
| 0461708 | 10/1968 | Switzerland | 604/89 |

Primary Examiner—C. Fred Rosenbaum
Assistant Examiner—Mark O. Polutta
Attorney, Agent, or Firm—Steinberg & Raskin

[57] ABSTRACT

An injection syringe for medical purposes, in which the syringe plunger or a plunger-side end of the syringe cylinder is shaped or provided with components to ensure at least one flow passage or connection between an inner cylindrical space of the cylinder and outer environment, when the plunger is partially, but not completely, introduced into the syringe cylinder.

5 Claims, 1 Drawing Sheet

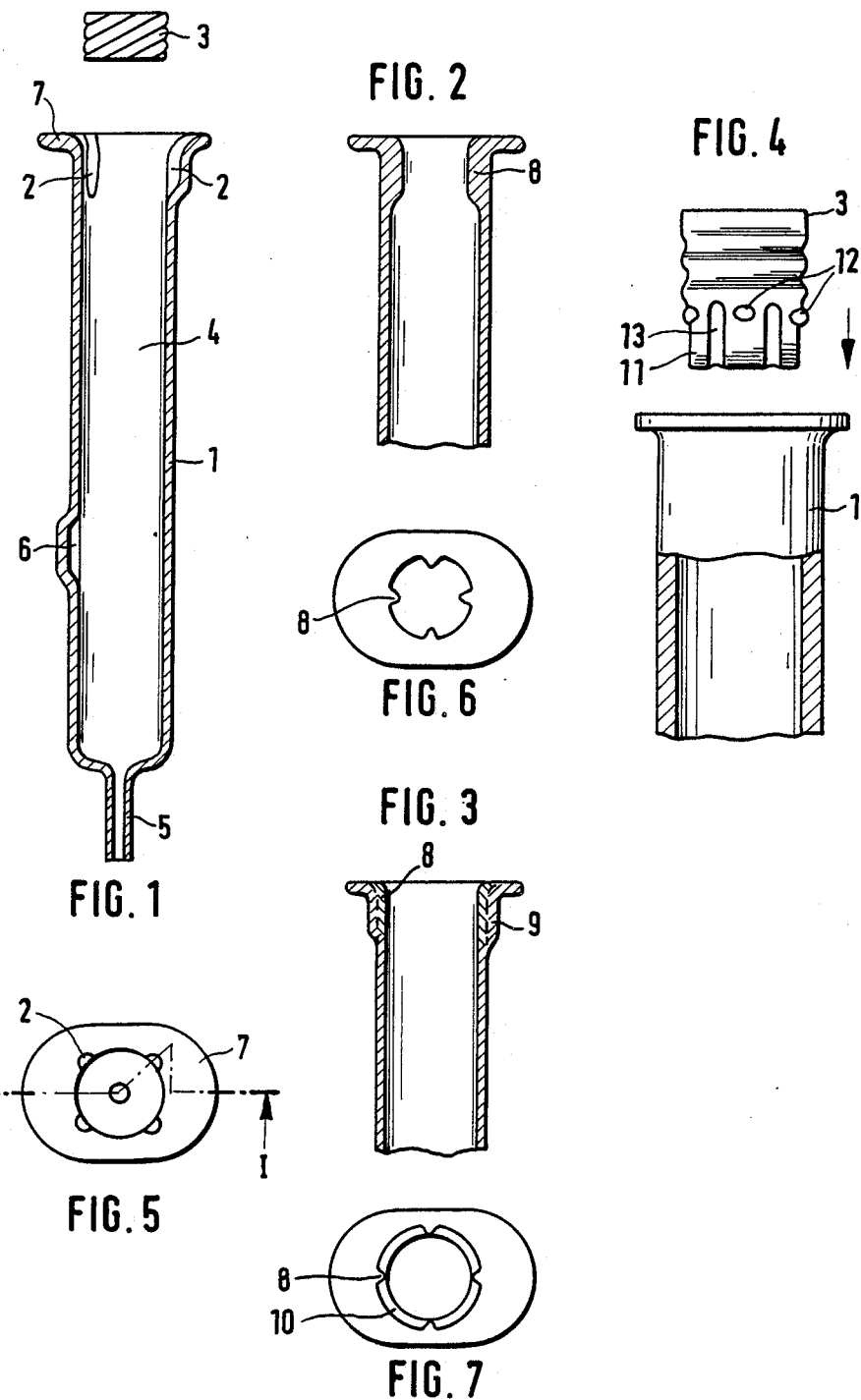

INJECTION SYRINGE FOR MEDICAL PURPOSES

BACKGROUND OF THE INVENTION

The present invention relates to an injection syringe for medical purposes, having a syringe cylinder and at least one displaceable syringe plunger, the cylinder having a needle attachment piece at one end thereof, and at an opposite end thereof an aperture for filling and for introducing the syringe plunger or plungers.

The syringe should, in particular, offer the possibility of drying medicine within the syringe in a vacuum or lyophilizing (freeze-drying) of the same. During freeze-drying, considerable quantities of solvent are drawn off in the vacuum, which means that the container in which the substance to be treated is contained, must have sufficiently large apertures through which the solvent vapor can escape.

Syringes of this type are known from European Patent Applications Nos. (examined) 0,191,122 and 0,144,483, and No. DE-OS 33-39-705. In these references, a solution to the above-noted problem which is suggested is a type of syringe which has a large aperture at its needle-side end which is only closed after the completion of the lyophilizing process by inserting a needle attachment piece.

A disadvantage in these syringe types, is that enclosing the finished lyophilized substance in the syringe takes place by inserting the needle attachment piece. In this process, several parts must be assembled for which elaborate technical operations are required which must be carried out in the sterile area of the production installation, since the syringe may only leave the sterile area when the lyophilized substance is tightly enclosed in the syringe.

SUMMARY OF THE INVENTION

Accordingly, it is an object of the present invention to provide a new and improved type of injection syringe.

It is also an object of the present invention to improve the design of a syringe over the above-described kinds in a manner such that medicine can be freeze-dried in the syringe, and the syringe containing lyophilized substance can be sealed in a simple manner in a freeze-drying installation, immediately after freeze-drying is completed, so that access of humidity to the lyophilized substance is prevented when the freeze-drying installation is opened.

These and other objects are attained by the present invention which is directed to an injection syringe having a cylinder and at least one displaceable plunger. The cylinder has a needle attachment portion mounted at one end thereof, and an aperture for introduction of the at least one plunger at an opposite end thereof. Means are provided at the plunger introduction end for ensuring at least one flow connection between an interior of the cylinder and outer environment when the at least one plunger is first inserted into the cylinder, but not completely introduced thereinto. Such means may comprise axially-extending channels or grooves sunk into an inner wall of the cylinder and opening toward the cylinder interior and toward an edge of the introducing aperture.

The present invention is also directed to an injection syringe plunger having means for ensuring at least one flow connection between an interior of a cylinder and outer environment when the plunger is partially inserted into the cylinder. This means comprise a short, substantially cylindrical attachment on the plunger of smaller diameter than diameter of the plunger in a region of a sealing bead thereon, and the attachment itself comprising at least three nub-like projections mounted on a circumference thereof at a location where the attachment joins the plunger proper. The projections are substantially equidistant from one another and are situated at substantially the same level along an axial length of the plunger, and also rise above the circumference of the attachment approximately as far as the sealing bead rises.

The above-noted and other objects are attained according to the present invention, in that means are provided either on a syringe plunger or on a plunger-side end of a syringe cylinder which, when the plunger is inserted but not completely introduced into the syringe cylinder, ensure at least one flow connection between an interior of the cylinder and outer environment.

Such a flow connection is preferably achieved by a short, substantially cylindrical attachment piece being attached to the syringe plunger, this attachment piece having a smaller diameter than a diameter of the plunger in a region of a bead. Furthermore, this attachment piece has, on a circumference thereof where the attachment widens to form the plunger proper, at least three nub-like projections substantially equidistant from one another and at substantially the same level along the attachment portion, with these projections also rising approximately as far above the circumference of the attachment piece as the sealing bead of the plunger itself.

The diameter of the cylindrical attachment piece is preferably about 10 to 25% smaller than the diameter of the plunger in the region of the sealing bead.

A syringe plunger of this nature with the noted cylindrical attachment piece, can be readily inserted into the plunger-side aperture of a normal injection syringe, and can be secured by exerting light pressure with the nub-like projections in the syringe end, so that between an inner wall of the syringe cylinder and the circumference of the plunger attachment piece, a marked annular gap remains, through which vapor can escape from the interior of the syringe during lyophilizing.

Connection between the inner space of the syringe and the outer atmosphere can be additionally improved by sinking at least two groove-like depressions in a peripheral surface of the plunger attachment piece and which extend axially and open or exit at a syringe-side end of the attachment piece. These groove-like depressions also end slightly past or above a plane of the nub-like projections, thus shortly below or before the first sealing bead of the plunger.

It is naturally also possible to provide axially-extending rib-like projections on the circumference of the plunger attachment piece instead of the nub-like projections, in order to secure the plunger with its attachment piece in the plunger-side end of the syringe cylinder.

In another embodiment, these flow connections are axially-extending channels or grooves sunk into an inner wall of the cylinder itself, and opening towards an inner space of the cylinder and towards an edge of the filling aperture, or even axially-extending ribs situated on the inner wall of the cylinder. These channels, grooves, or ribs, are preferably a little shorter than the height or length of the plunger itself. However, these channels, grooves, or ribs are not significantly shorter than the height of the plunger, i.e. the height or length of the plunger sealing surface. This is particularly so in the case of a so-called two-chambered syringe which has at least one bypass between the chambers which is activated the moment the plunger separating the two chambers is pushed into the region of the bypass, so that mixing of the contents of the two syringe chambers becomes possible across the bypass and past the intermediate plunger.

The bypass in the wall of the syringe cylinder must not extend strictly axially. It can also be arranged at an angle of approximately 10° to 45° with respect to the axial direction. Thus, the bypass can extend in the cylinder wall to be inclined with respect to the longitudinal direction of the syringe, so that the fluid from the second chamber does not shoot directly towards the needle-side end of the syringe, but rather runs in spiral fashion along the inner wall of the syringe and better mixes with the content of the first chamber.

The channels, grooves or ribs at the plunger-side end of the syringe, are so formed that the syringe plunger or the intermediate plunger which, in the case of a two-chambered syringe, separates the two chambers from one another, can be inserted into the syringe after the substance to be freeze-dried has been filled therein. Thus, the plunger is positioned and perfectly held in the plunger-side end of the syringe, and largely closes this wide aperture. However, on the other hand, escape of vapor which is released during the freeze-drying from the interior of the syringe in this end region of the cylinder wall of the syringe across the channels or grooves and past the inserted plunger, is possible.

An analogous effect can be achieved through axially-extending short rib pieces which are arranged at the plunger-side end of the syringe cylinder, if the height of the ribs and the hardness of the plunger material are so adjusted with respect to one another that the elastic material of the plunger does not entirely rest on the side walls of the ribs, on the base of the ribs, and on the inner wall of the cylinder, so that air slits remain parallel to the ribs. These air slits are closed the moment the syringe plunger is pushed somewhat further into the syringe cylinder, beyond the region which has the channels, grooves or ribs.

The plunger-side end of the syringe cylinder can, however, also be structured so that these ribs do not rise above the inner wall of the cylinder, but represent a straight extension of the inner wall of the cylinder and instead widen the inner wall of the cylinder in this region by an amount which represents the height of the ribs. Therefore, when the plunger is inserted and is retained by the ribs, an annular interspace is formed between the outer wall of the plunger and the inner wall of the syringe cylinder in this end region of the syringe cylinder, through which vapor of the syringe contents can be drawn off during freeze-drying. In this case too, the ventilation possibility is closed the moment the plunger is pushed beyond the end region and somewhat deeper into the cylinder, so that the plunger rests on the entire inner wall of the cylinder.

The design according to the present invention of a lyophilization syringe, in particular a two-chambered syringe, has the advantage that a syringe cylinder with a completely prepared needle attachment of conventional design and also a two-chambered syringe, with a conventional bypass, can be utilized. The needle attachment may have a so-called Luer cone which may be closed with a cap and/or a filter inset. If such a syringe body is filled with the medicinal component to be lyophilized, then the syringe can be handled in the customary manner in the freeze-drying installation, and outside of the installation with the needle-side end hanging downwardly. After completion of the freeze-drying process, the syringe can be tightly closed in the freeze-drying installation by lightly pressing the plunger which is already inserted in the syringe cylinder, so that all subsequent manipulation can be carried out outside the freeze-drying installation, without changing the degree of dryness of the lyophilized substance through access of air.

BRIEF DESCRIPTION OF THE DRAWINGS

The present invention will be further described below in greater detail, with reference to several embodiments illustrated according to the following figures, in which FIG. 1 is a longitudinal sectional view along line I—I in FIG. 5 through a two-chambered syringe according to the present invention;

FIG. 2 is a partial, longitudinal sectional view through a syringe end piece according to the present invention and having integrally formed ribs;

FIG. 3 is a partial, longitudinal sectional view of a further embodiment of a syringe end piece according to the present invention;

FIG. 4 is a lateral view illustrating a syringe plunger according to the present invention and immediately therebelow, a plunger-side end of a conventional injection syringe, partially in axial section;

FIG. 5 is a top view of the plunger-side end of the syringe illustrated in FIG. 1;

FIG. 6 is a top view of the plunger-side end of the syringe illustrated in FIG. 6; and FIG. 7 is a top view of the plunger-side end of the syringe illsutrated in FIG. 3.

DESCRIPTION OF THE PREFERRED EMBODIMENTS

FIGS. 1 and 5 respectively illustrate sectional and top views of a plunger-side end of a lyophilization syringe according to the present invention. Several channels or grooves 2 are sunk into the plunger-side end of a cylinder 1, and open towards an inner space 4 of the cylinder 1, as well as opening toward a filling aperture 7. These channels or grooves 2 run axially and extend a short distance in the direction of the needle-side end of the syringe. They are approximately as long as the plunger 3 is high, preferably a little shorter than the height of the plunger 3. In a so-called two-chambered syringe illustrated in FIG. 1, the length of the channels or grooves 2 is adjusted to a height of a so-called intermediate plunger 3, which means a plunger that is inserted to separate a first chamber from a second chamber and situated slightly above a bypass 6 in the cylinder 1, after the first component is filled into the first chamber of the cylinder. The syringe itself, may have a conventional needle attachment 5, for example a Luer cone, which may have a conventional closure cap and/or a filter inset of filter top.

The syringe may be charged, for example, with medicinal solution in a conventional filling device in which the syringe-side end hangs downwardly, and then subsequently provided with a conventional plunger 3. At this stage, the plunger 3 is inserted into the syringe cylinder for only a limited distance, so that ends of the channels 2 leading into the syringe are still exposed, i.e., not covered by the plunger 3. In this state, i.e. with a closed needle attachment, filled with lyophilization substance, and with attached plunger 3, the syringe is transferred to the freeze-drying installation. The vapor drawn during freeze-drying from the lyophilization substance, escapes across channels 2 and past the plunger 3. As soon as the freeze-drying process is completed, the plunger is then pushed into the syringe cylinder so far that the channels 2 are closed. If the channels 2 are somewhat shorter than the height of the plunger 3, then this closure is already achieved by the plunger 3 being pushed flush with the syringe end by bringing setting plates of the freeze-drying installation closer together. The syringe can be removed from the freeze-dryer in this state.

In the case of a two-chambered syringe, the intermediate plunger is pushed further into the interior of the syringe after removing the syringe from the freeze-drying installation, to a point closely above the location where the bypass 6 ends. Subsequently, a second component, most often a solvent for the lyophilized substance, is filled in, and the injection plunger is then inserted.

In the embodiment illustrated in FIGS. 2 and 6, positioning and securing of the plunger 3 and ventilating of the cylinder space 4, is achieved by providing short ribs 8 at a plunger-side end.

These ribs 8 can either rise above an inner wall of the cylinder 1, or can be aligned with the inner wall of the cylinder as illustrated in FIGS. 3 and 7. In the embodiment illustrated in FIGS. 2 and 6, the plunger 3 is deformed by the projecting ribs 8 during insertion. Thus, the plunger 3 does not completely rest upon the side walls of the ribs 8. On both sides of each rib 8, parallel to the rib 8, air slits remain which connect the interior space 4 with the surrounding space, as long as the plunger 3 is not completely inserted into the syringe end. The outer diameter of the plunger 3 must naturally correspond at least to the inner diameter of the syringe cylinder 1 without the ribs 8. The plunger 3 can have a short attachment 11 of smaller diameter, with which the plunger 3 can be readily inserted into the syringe end and can be positioned and secured between the ribs 8. The vapor can escape from the syringe during freeze-drying through the annular gap between the outer wall of the short attachment 11 to the plunger 3 and the inner wall of the syringe end.

The embodiment illustrated in FIGS. 3 and 7 is advantageous, in which the ribs 8 represent a continuation of the inner cylinder wall 1, and the inner cylinder wall 1 is widened in an end region 9 so that an annular space 10 originates when the plunger 3 is inserted therein, through which vapor can escape from the interior of the syringe during freeze-drying.

The same dimensions and ratio of length to the plunger 3 apply for the ribs 8, as for the channels or grooves 2 in the preceding embodiment illustrated in FIGS. 1 and 3. In other words, the ribs 8 are also somewhat shorter than height of the plunger 3, and extend axially towards an interior of the cylinder 1, and towards an edge of the filling aperture 7 as illustrated in FIGS. 2 and 3. The plunger 3 is also manipulated with respect to the cylinder 1 in the same manner, as described with respect to FIGS. 1 and 3.

The number of channels 2 or ribs 8 depends on the through capacity and the amount of vapor to be drawn off. As a rule, the number of channels 2 or ribs 8 will be between about 3 and 8, preferably between about 3 and 5.

A plunger can be advantageously used as a separation plunger between the two chambers of a two-chambered syringe, which has oblique perforations in a sealing lip facing the lyophilized substance, and an annular intermediate space of small depth between the sealing lip and a subsequent sealing lip (i.e. between an inner cylinder wall and the outer plunger wall). Such a plunger functions as a distributor for the solvent, if the solvent, upon activation of the syringe, enters into the region of the bypass 6 and into the annular intermediate space and through the oblique perforations exits into the lyophilized substance.

The embodiment illustrated in FIG. 4 is especially advantageous, because a conventional, unmodified syringe cylinder can be used in this embodiment. In this case, the plunger 3 is provided with a cylindrical attachment 11 of smaller diameter. The diameter of the attachment 11 is approximately 10 to 25% less than the diameter of the plunger in a region of a sealing bead. Hence, the diameter of the attachment 11 is also less than an inner cylinder of the syringe cylinder 1.

The plunger 3 is secured with this attachment 11 into the plunger-side end of the syringe cylinder 1, with the aid of nub-like projections 12. The plunger 3 is pushed into the end of the cylinder 1 only far enough so that the nub-like projections 12 engage an inner edge of the cylinder 1. In this position, an annular gap remains between the attachment 11 and an inner wall of the syringe cylinder. During lyophilizing, vapor can escape from the interior of the syringe through this annular gap.

The plunger provided with such attachment can have one to three sealing beads. If the plunger is to be used in a two-chambered syring, then the sealing length must naturally be somewhat shorter than the bypass 6 in the syringe wall. The plunger shown in FIG. 4 has, in addition, groove-like depressions 13 extending axially in a circumference of the attachment 11, in order to improve ventilation of the inner cylinder space when the plunger 3 is attached.

In this case too, the plunger 3 must not be pushed so far into the syringe end that the first sealing bead closes the annular gap of the ventilation channels 13.

The syringe according to the present invention offers significant advantages during lyophilizing as compared to known lyophilization syringes which are open at the needle-side end and which must be closed after lyophilization by inserting a needle attachment which requires cumbersome operations under sterile conditions. In contrast, in the syringe according to the present invention, slightly pressing the plunger 3 into a flush position with the plunger-side end of the syringe suffices in order to close the syringe, after completion of the freeze-drying.

The preceeding description of the present invention is merely exemplary, and is not intended to limit the scope thereof in any way.

What is claimed is:

1. Injection syringe plunger having means for ensuring at least one flow connection between an interior of a cylinder and outer environment when the plunger is partially inserted into the cylinder, wherein said means comprise a short, substantially cylindrical attachment on the plunger of smaller diameter than the diameter of the plunger in a region of a sealing bead thereon, said attachment comprising at least three, projections mounted on a circumference thereof at a location where said attachment joins the plunger proper, and said projections being substantially equidistant from one another and situated at substantially the same level along an axial length of the plunger, and rising above the circumference of said attachment approximately as far as the sealing bead.

2. The combination of claim 1, wherein said means additionally comprise at least two groove-like depressions extending axially along the circumference of said attachment, opening at an end of said attachment opposite the plunger proper, and ending slightly past the location of said projections on the plunger.

3. The combination of claim 1, wherein the diameter of said attachment is about 10 to 25% smaller than the diameter of the plunger in the region of the sealing bead.

4. The combination of claim 1, wherein said projections are nub-like in shape.

5. The combination of claim 1, wherein said projections axially extend along the circumference of said attachment and are rib-like in shape.

* * * * *